(12) United States Patent
Bishop et al.

(10) Patent No.: US 7,918,824 B2
(45) Date of Patent: Apr. 5, 2011

(54) NEEDLED PHARMACEUTICAL DELIVERY DEVICE WITH TRIGGERED AUTOMATIC NEEDLE INSERTION AND MANUALLY CONTROLLED PHARMACEUTICAL INJECTION

(75) Inventors: Steven Bishop, Mountain View, CA (US); Adrian Benton James, Palo Alto, CA (US); John W. Lai, San Bruno, CA (US); Robert Ian Lister, Sunnyvale, CA (US); Nancy J. Serpiello, Emerald Hills, CA (US)

(73) Assignee: Eli Lilly and Company, Indianapolis, IN (US)

( * ) Notice: Subject to any disclaimer, the term of this patent is extended or adjusted under 35 U.S.C. 154(b) by 513 days.

(21) Appl. No.: 11/915,859

(22) PCT Filed: Jun. 19, 2006

(86) PCT No.: PCT/US2006/023930
§ 371 (c)(1),
(2), (4) Date: Nov. 29, 2007

(87) PCT Pub. No.: WO2007/002053
PCT Pub. Date: Jan. 4, 2007

(65) Prior Publication Data
US 2009/0312707 A1 Dec. 17, 2009

(51) Int. Cl.
*A61M 5/20* (2006.01)
(52) U.S. Cl. .......... 604/136; 604/197; 604/198
(58) Field of Classification Search ............ 604/110, 604/134–137, 192, 198, 131, 187, 197
See application file for complete search history.

(56) References Cited

U.S. PATENT DOCUMENTS

| 361,750 | A | 4/1887 | Dunbar |
| 922,331 | A | 5/1909 | Quarles et al. |
| 2,664,086 | A | 12/1953 | Transue |
| 2,804,074 | A | 8/1957 | Hill |
| 3,605,742 | A | 9/1971 | Tibbs |
| 3,605,743 | A | 9/1971 | Arce |
| 3,612,051 | A | 10/1971 | Arce |
| 4,270,537 | A | 6/1981 | Romaine |

(Continued)

FOREIGN PATENT DOCUMENTS

GB 969781 A 9/1964

(Continued)

*Primary Examiner* — Theodore J Stigell
(74) *Attorney, Agent, or Firm* — Edward J. Prein (57) ABSTRACT

A pharmaceutical delivery device with triggered automatic needle insertion and manually controlled pharmaceutical injection. The pharmaceutical delivery device includes a housing, a pharmaceutical containing needled syringe having an injection tip that is recessed within the housing when the syringe is in a first position and which projects from the housing when the syringe is in a second position, a syringe advancing assembly operable to automatically advance the needled syringe from the first position to the second position, a plunger including an input portion projecting from the housing for manual access by a user, wherein the plunger is operable by the user directly shifting the input portion when the syringe is disposed in the second position to inject pharmaceutical from the syringe through the needle at a rate adjustably controlled by a user during the injection, and wherein the plunger includes a plunger extender automatically movable within the housing from a first location to a second location upon the needled syringe advancing from the first position to the second position, wherein the plunger extender, when in the second location, occupies a space vacated by the needled syringe during advancement from the first position to the second position, whereby the plunger input portion remains stationary relative to the housing during the advancement of the needled syringe.

7 Claims, 5 Drawing Sheets

U.S. PATENT DOCUMENTS

| | | |
|---|---|---|
| 5,114,404 A | 5/1992 | Paxton et al. |
| 5,267,963 A | 12/1993 | Bachynsky |
| 5,320,609 A | 6/1994 | Haber et al. |
| 5,425,715 A | 6/1995 | Dalling et al. |
| 5,514,097 A | 5/1996 | Knauer |
| 5,540,664 A * | 7/1996 | Wyrick .................. 604/136 |
| 5,665,071 A | 9/1997 | Wyrick |
| 5,695,472 A | 12/1997 | Wyrick |
| 5,980,491 A | 11/1999 | Hansen |
| 2005/0277885 A1 | 12/2005 | Scherer |

FOREIGN PATENT DOCUMENTS

| | | |
|---|---|---|
| WO | WO 2005/115512 A | 12/2005 |
| WO | WO 2005/115516 A | 12/2005 |

* cited by examiner

NEEDLED PHARMACEUTICAL DELIVERY DEVICE WITH TRIGGERED AUTOMATIC NEEDLE INSERTION AND MANUALLY CONTROLLED PHARMACEUTICAL INJECTION

BACKGROUND OF THE INVENTION

The present invention pertains to pharmaceutical delivery devices, and, in particular, to a pharmaceutical delivery device having an automatic needle insert.

Patients suffering from a number of different diseases frequently must inject themselves with pharmaceuticals. As some patients find it difficult to insert a needle of an injector into one's skin, a variety of devices have been developed to facilitate this insertion task.

One type of such device automatically inserts a needle and then automatically injects a dose of medication through the inserted needle. With one version of this type device, after unlocking the device by manually twisting a handle, a patient needs to position the device against an injection site, and then operate a trigger of the device, such as by pressing the device firmly against the site. Trigger operation first causes a needled syringe within a housing of the device to shift such that its needle penetrates the skin, and then without further trigger operation or other user input, automatically causes a piston within the syringe to move to force the syringe contents through the inserted needle and into the patient. While this type of device may be useful for some patients, other patients may object to lacking control of the rate at which the injection process occurs.

Another known device disclosed in U.S. Pat. No. 5,980,491 mounts an injection pen therein and allows the needle of that pen to be automatically inserted into an injection site, whereafter the injection pen can be manually controlled to inject medication at a desired rate. However, because during needle insertion the injection pen is driven axially relative to the device, the patient may be startled or uncomfortable with the visible shifting of the pen, and further may have to readjust his or her hand to properly position a digit over the pen plunger before manually controlling the injection.

Thus, it would be desirable to provide a device that can overcome one or more of these and other shortcomings of the prior art.

BRIEF SUMMARY OF THE INVENTION

In one form thereof, the present invention provides a pharmaceutical delivery device including a housing having a first end and a second end spaced in an axial direction, a pharmaceutical containing needled syringe mounted within the housing to be movable in the axial direction from a first position to a second position, wherein an injection tip of the syringe needle is recessed within the housing when in the first position and projects from the housing beyond the first end when in the second position, a syringe advancing assembly operable to automatically advance the needled syringe from the first position to the second position, and a plunger including an input portion projecting from the housing for manual access by a user, wherein the plunger is operable by the user directly shifting the input portion when the needled syringe is disposed in the second position to inject pharmaceutical from the syringe through the needle at a rate adjustably controlled by a user during the injection. The plunger also includes a plunger extender automatically movable within the housing from a first location to a second location upon the needled syringe advancing from the first position to the second position. The plunger extender, when in the second location, occupies a space vacated by the needled syringe during advancement from the first position to the second position, whereby the plunger input portion remains stationary relative to the housing during the advancement of the needled syringe.

One advantage of the present invention is that a pharmaceutical delivery device having automatic needle insertion, manual dose injection operability may be provided that is easy and intuitive to operate.

Another advantage of the present invention is that a pharmaceutical delivery device with automatic needle insertion may be provided in which its user controlled injecting plunger remains stationary relative to the device housing during needle insertion.

Yet another advantage of the present invention is that a pharmaceutical delivery device may be provided in which an automatic insertion of the device needle is performed by pressing toward an injection site a button disposed on another portion of the device most distant from the injection site.

Yet another advantage of the present invention is that a pharmaceutical delivery device may be provided in which a trigger button for an automatic needle insertion is disposed on the plunger for manually controlling injection, whereby both the button and plunger can be operated without a user needing to change her hand position.

BRIEF DESCRIPTION OF THE DRAWINGS

The above-mentioned and other advantages and objects of this invention, and the manner of attaining them, will become more apparent, and the invention itself will be better understood, by reference to the following description of embodiments of the invention taking in conjunction with the accompanying drawings, wherein.

Corresponding reference characters indicate corresponding parts throughout the several views. Although the drawings represent an embodiment of the present invention, the drawings are not necessarily to scale, and certain features may be exaggerated or omitted in some of the drawings in order to better illustrate and explain the present invention.

DETAILED DESCRIPTION OF THE INVENTION

Figure 1:
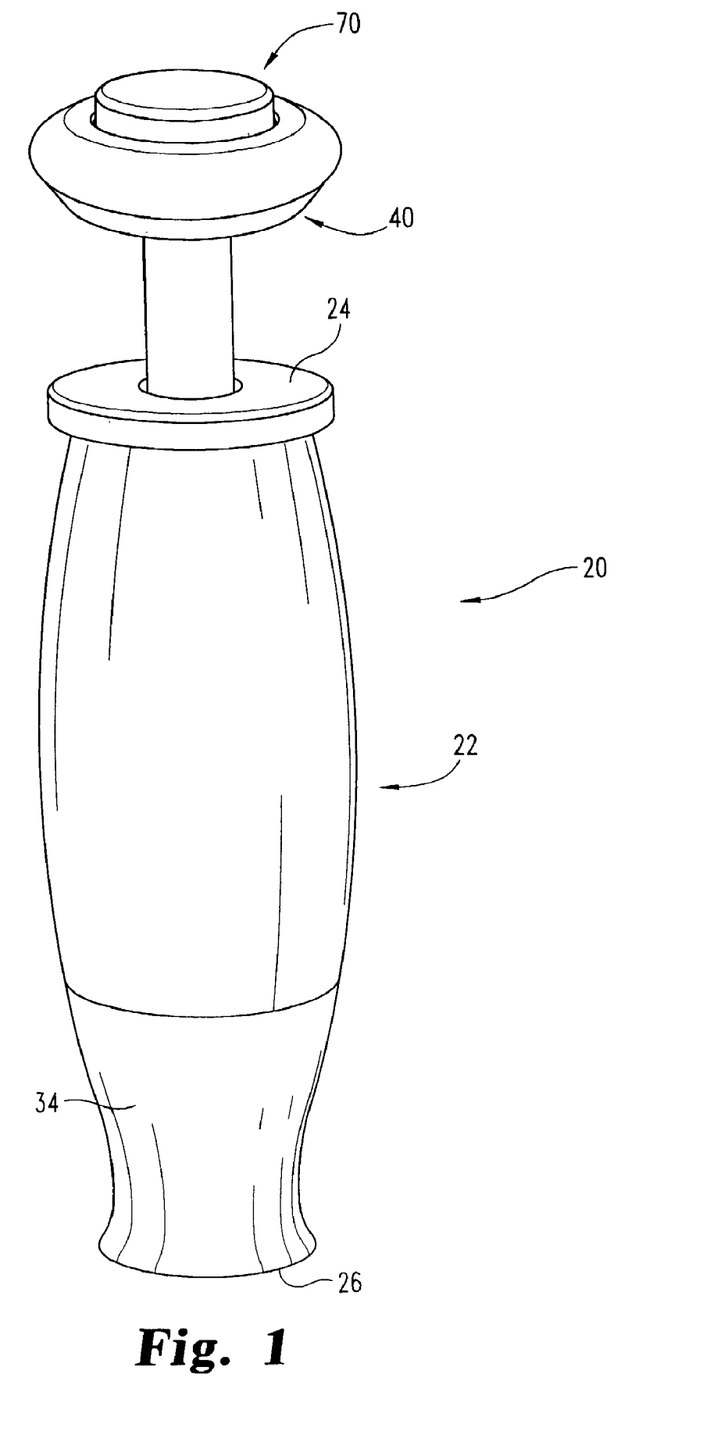
FIG. 1 is a front perspective view of a pharmaceutical delivery device of the present invention, which device is shown arranged in a ready to insert configuration.

Referring now to FIG. 1, there is shown a first embodiment of a pharmaceutical delivery device of the present invention. Any directional references in this detailed description with respect to FIG. 1 or any of the other Figures, such as up or down, or top or bottom, are intended for convenience of description, and by itself does not limit the present invention or any of its components to any particular positional or spatial orientation.

The delivery device, generally designated 20, includes an outer housing, generally designated 22, having a distal end 24 and a proximal end 26. As used herein, distal and proximal refer to axial locations on the delivery device relative to an injection site when the device is oriented for use at such site, whereby, for example, proximal end of the housing refers to the housing end that is closest to such injection site.

Outer housing 22 includes a cylindrical tubular body 30, a cap member 32, and a needle shield 34. Body 30 is made of plastic and has an interior hollow 38 that extends longitudinally or axially, in which axial direction the syringe is driven during needle insertion. Body 30 has a radial periphery covered with a resilient gripping layer 31 made of a softer material and with a convex contour which facilitates the housing being grasped more comfortably and reliably within the hand of a user. Cap member 32, which is securely attached to body 30 during manufacture in a suitable fashion, forms the housing distal end 24. Cap member 32 is made of plastic and includes a central opening through which a plunger shaft is movable axially. Housing 22 and a plunger, generally designated 40, are keyed together in a suitable fashion to be rotatably fixed together, such as via a keying of shaft 46 with body 30. Plunger 40 and cap member 32 further are complementarily configured, such as via a not shown step-downed neck of the plunger shaft around which a two-piece cap member 32 is installed during manufacture, to prevent plunger 40 from being completely withdrawn from within the housing after manufacture. Needle shield 34 is made of plastic with a tapering contour and a flared proximal end. Needle shield 34 may be transparent to allow the injection site and the needle tip to be observed by a user, and further may have a colored circle or a cross-hair design around the opening 35 to help a user observe an injection site. Opening 35 allows needle 115 to pass therethrough and pierce the injection site against which the proximal face of the needle shield has been placed for administration of the medication.

Plunger 40 is molded from plastic and includes an enlarged, disc or cylindrical shaped head 42, and a tubular, cylindrical shaft 46 that depends from the proximal face 43 of head 42. Head 42 and the distal portion of shaft 46 project distally beyond the distal end of housing 22, and head 42 is manually pressable by a user to plunge the plunger 40 to cause an injection as described further below. Shaft 46 includes an interior bore 48 within its distal region that open into a cylindrical hollow 45 formed into the distal face 44 of head 42. Shaft 46 includes a reduced diameter portion 50 at its proximal end, and the proximal region 49 of the larger diameter shaft portion includes an annular bore or hollow 52. The proximal end of shaft region 49 has an inturned lip 54 that forms a supportive shoulder for the proximal end of a biasing member 56, such as a metal coiled spring, that serves as a reset spring for the reloadable device shown. Plunger portions 42, 46 and 50 may be formed together in one piece.

The distal end of spring 56 abuts an outturned lip 62 of an extender portion of the plunger, generally designated 60. Plunger extender 60 is molded of plastic and includes a tubular barrel 64 with a closed proximal end face that fits within a syringe to directly contact a syringe piston for advancement. Barrel 64 is rotatably fixed with and telescopically fits over reduced diameter shaft portion 50, and is sized to axially slide therealong and within the annular space between shaft portion 50 and shaft lip 54. Plunger extender 60 includes a not shown latching module that engages a corresponding, not shown latching module of shaft 46, such as a module on shaft portion 50, when plunger extender 60 has finished being shifted proximally relative to shaft 46 during needle insertion as described further below. Any suitable latching module known in the art may be employed, such as one or more resilient finger(s) with a latching nub(s) of one of the shaft or plunger extender fitting into or over a nub-receiving opening(s) or recess(es) or end face of the other of the shaft or plunger extender.

Figure 2:
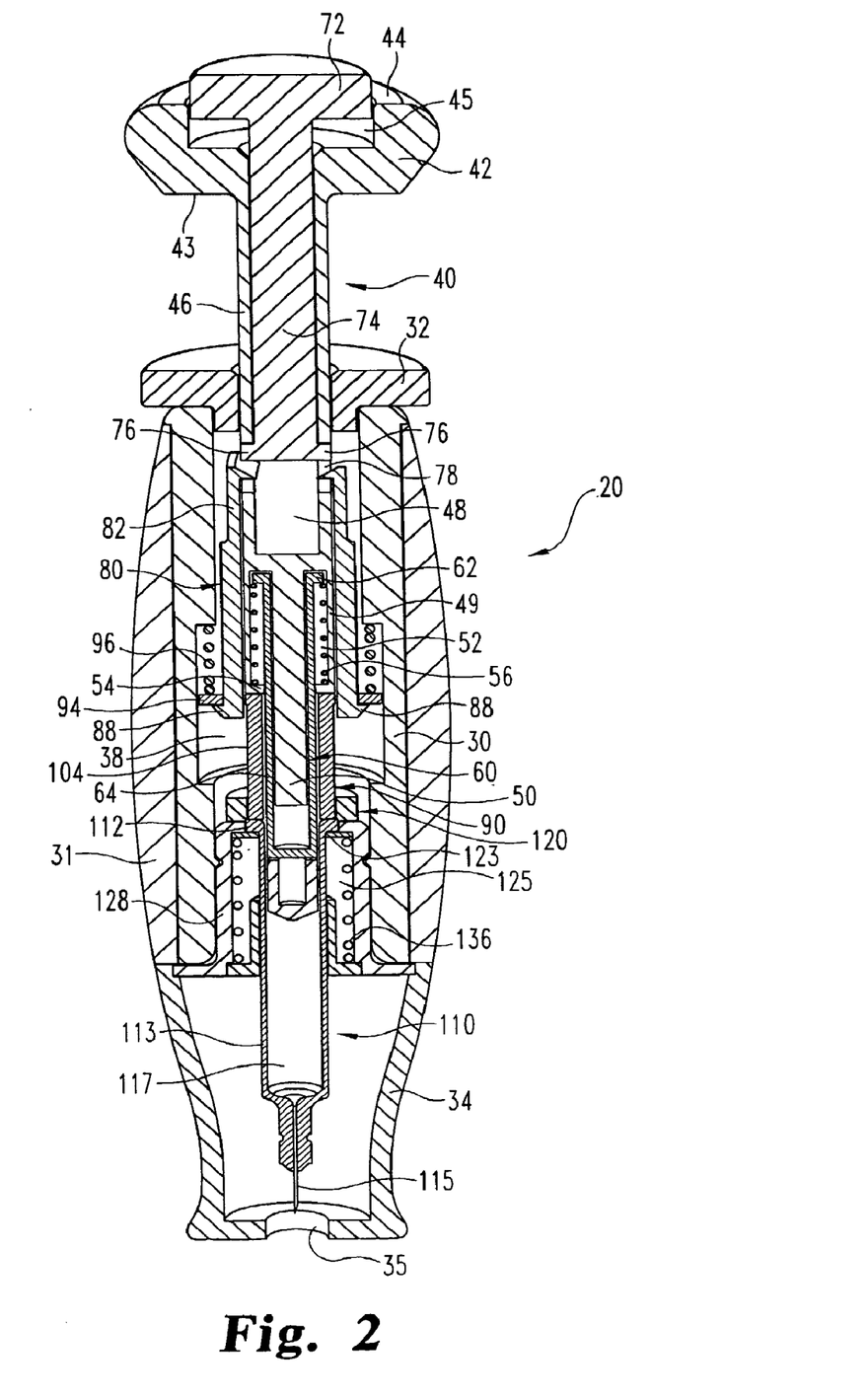
FIG. 2 is a longitudinal cross-sectional view of the delivery device of FIG. 1.
Figure 3:
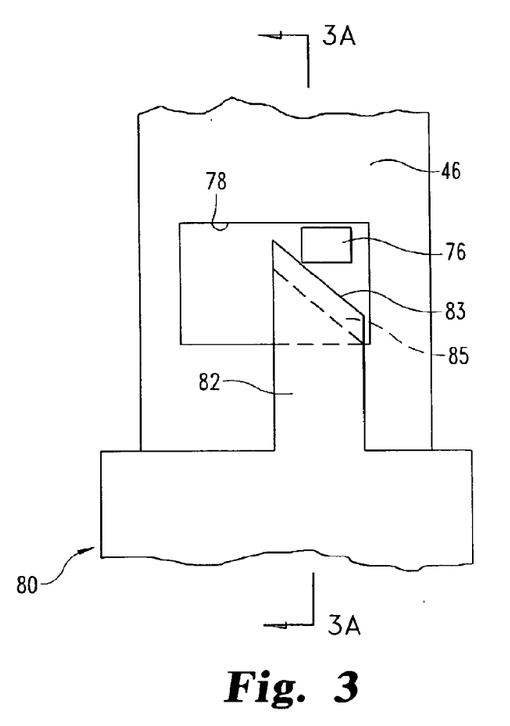
FIG. 3 is a diagrammatic, partial side view of the plunger shaft, trigger, and lock sleeve of the delivery device of FIG. 1, wherein such components are shown free of all the other device components.

An axially plungable trigger for needle insertion, which trigger is generally designated 70, is molded in one piece from plastic and includes enlarged head 72 and shaft 74. Head 72 is disc or button-shaped and disposed at the distal end of device 20 for convenient manual access by a user. Head 72 is sized-to fit within hollow 45. Shaft 74 depends from the proximal face of trigger button 72 and slidably fits within plunger shaft bore 48. Trigger 70 is rotatably fixed within plunger 40, such as via a keying of plunger shaft 46 with trigger shaft 74. At the proximal end of shaft 74, a pair of diametrically opposed tabs 76 radially outwardly project and fit within a pair of diametrically opposed openings 78 formed in plunger shaft 46. Not shown relief notches allow the tabs 76 to flex inwardly during assembly of the trigger to the plunger shaft. Openings 78 and tabs 76 define the possible range of axial motion of trigger 70 relative to plunger shaft 46. In the ready to insert arrangement of the device shown in FIG. 2, tabs 76 are disposed in abutting engagement with the distal edge of openings 78, resulting in the button 72 protruding partially out of plunger hollow 45, whereby the distal face of button 72 is positioned slightly distally of distal face 44 of plunger 40. To trigger needle insertion, button 72 is plunged proximally relative to plunger shaft 46 and housing 22. After button 72 is so plunged, and as shown in FIG. 3, tabs 76 are disposed adjacent with the proximal edge of openings 78, such that button 72 fits within plunger hollow 45 with its distal face in substantially coplanar relationship with plunger distal face 44. To keep trigger 70 from floating within plunger 40 both before and after trigger plunging, suitable locating mechanisms, such as indents and corresponding detents on such elements, may be provided.

Figure 3A:
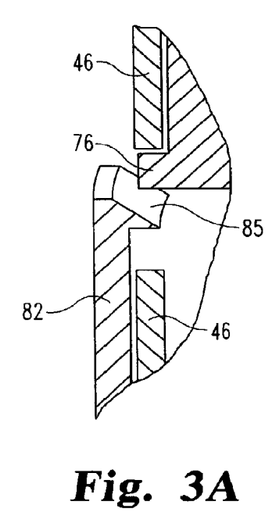
FIG. 3A is a cross-sectional view taken along line 3A-3A of FIG. 3.
Figure 4:
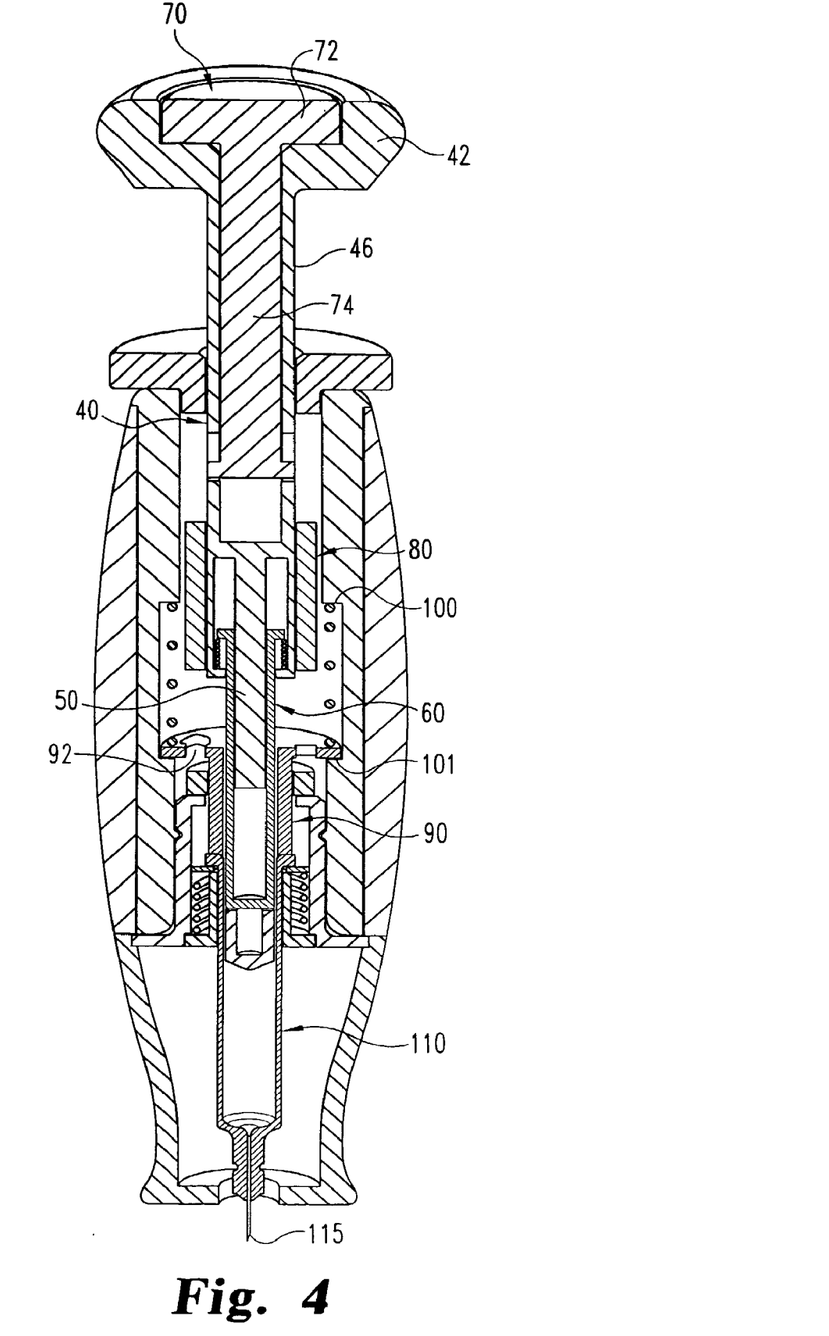
FIG. 4 is a view of the delivery device of FIG. 2 after its automatic needle insertion function has been completed, whereby the device is shown arranged in a ready to inject configuration.

A lock sleeve 80 made of plastic is disposed within body hollow 38 between the interior surface of body 30 and the exterior surface of plunger shaft 46. Lock sleeve 80 is keyed to body 30 in a not shown manner to be axially fixed within body 30, but to be rotatable in body 30 within an angular range required to unlock an insertion sleeve 90. One suitable range of angular motion is about 30°. As further shown diagrammatically in FIGS. 3 and 3A, the distal end region of lock sleeve 80 includes two diametrically opposed resilient, distally projecting fingers 82 each with a ramp 83 at a distal end. The distal face of each ramp 83 is inclined at 85 to facilitate its finger 82 being cammed outward by plunger shaft 46 when shaft 46 is plunged proximally to cause an injection. Although two fingers, and corresponding trigger tabs 76 and plunger shaft openings 78, are shown, additional such components or as few as one of each such component, may be employed within the scope of the present invention.

Each ramp 83 is designed to be abutted by a trigger tab 76. During this abutting contact, as the trigger button is manually pressed downwardly relative to handle 40 to initiate needle insertion, the downwardly moving trigger tab 76 forces lock sleeve 80 to rotate due to ramp 83 sliding under and along trigger tab 76 until a complete button plunging has occurred. For the reusable delivery device shown, the slope of the lock sleeve ramps are selected to be back drivable so as to force the trigger tabs 76, and therefore the entire trigger, distally during reset of the device as described further below.

At its proximal end, lock sleeve 80 includes at least one latching module for engaging a complementary latching module of the insertion sleeve 90 to releaseably lock the sleeves together axially when in a certain arrangement. In the shown embodiment, the latching module of lock sleeve 80 includes a pair of diametrically disposed latches 88 that depend from the proximal end of lock sleeve 80. Latches 88 are sized and shaped to cooperate with corresponding slots 92 formed in an annular collar 94 of insertion sleeve 90.

Insertion sleeve 90 is molded from plastic and keyed with body 30 to be axially movable and rotatably fixed relative thereto. Slots 92 are arcuate with a center of curvature along the central axis of the device. Slots 92 are shaped to have collar 94 be axially secured by latches 88 when sleeves 80 and 90 are in a first relative rotational arrangement, and to have collars 94 not be axially secured by latches 88 when sleeves 80 and 90 are in a second relative rotational arrangement. Although not shown in the figures, the distal face of collar 94, for the reloadable delivery device shown, is provided with camming members that engage the lock sleeve latches 88 so as to cause appropriate rotation of the lock sleeve during apparatus reset to reengage the latching connection between the lock sleeve and insertion collar.

The region of insertion sleeve collar 94 radially inward of slots 92 serves as a stop face for abutting contact with the lip 54 of plunger shaft 46. This abutting contacts stops plunger 40 from being plunged prior to the activation of trigger 70, which trigger activation results in insertion sleeve 90 shifting proximally, until the proximal face of sleeve 90 abuts shoulder 101 of body 30, so as to allow a subsequent plunging of plunger 40. The end of plunger travel during injection is also defined by abutting contact of plunger 40 with the shifted collar 94. The region of collar 94 radially outward of slots 92 is abutted by the proximal end of a biasing member 96, such as a metal coiled spring, that drives the needle insertion. The distal end of biasing member 96 abuts a shoulder 100 of body 30, whereby spring 96 tends to bias insertion sleeve 90 proximally relative to housing 22.

The proximal end 102 of insertion sleeve 90 is opened and allows plunger extender 60 to pass therethrough. Proximal end 102 is sized to abut and thereby directly engage the distal, lipped end 112 of the medication containing needled syringe, generally designated 110, to drive syringe 110 proximally through housing 22 to effect needle insertion. The interior of insertion sleeve 90 and the exterior of plunger extender 60 are complementarily configured, for example with one or more grooves and followers, such that insertion sleeve 90 drives motion of plunger extender 60 in an identical distance and direction as the proximal motion of insertion sleeve 90 relative to the housing during the spring-driven insertion sleeve advancement from the arrangement shown in FIG. 2 during needle insertion, such that the axial space, if any, between the proximal face of plunger extender 60 and syringe piston is held constant during syringe advancement. The sleeve/extender complementary configuration also allows plunger extender 60 to shift proximally relative to insertion sleeve 90, such that the depressing of head 42 of plunger 40 to inject can drive such plunger extender portion of the plunger proximally an equal amount as the motion of head 42 to effect syringe piston advancement.

Syringe 110 is of known design and includes a glass barrel 113, an injection needle 115 projecting from the proximal end of barrel 113 and porting to the proximal end of the medicine-containing reservoir within the barrel interior volume 117, and a piston slidably and sealingly located at the distal end of the reservoir. In the shown embodiment, syringe 110 is removably mounted within a resilient washer 123 that frictionally engages the exterior periphery of glass barrel 113. Washer 123 is sized to slide within a cylindrical hollow 125 of a plastic cup-shaped element 128 having a flared lip 130 which is fixably secured to housing needle shell, as well as to a plastic cap piece 133. A dampening spring 136 made of metal has a distal end which abuts the washer 123, and a proximal end that abuts cap piece 133. The shell, cup element 128, cap piece 133 and spring 136 and washer 123 together form a removable subassembly, generally designated 150, in the shown embodiment. A projecting collar 138 of cap piece 133 is disposed inward of spring 136 and slidably accommodates glass barrel 113 to maintain the axial orientation of syringe 110 during needle insertion. The exterior periphery of cup 128 includes a circumferential recess 140 that is engaged by circumferentially spaced ribs 142 on the radially inward facing surface of body 30. Recess 140 and ribs 142 allow for a snap fit attachment of subassembly 150 to body 30, which attachment can be overcome for syringe replacement. Other forms of attachment, such as a screw type connection, alternatively may be employed.

Figure 5:
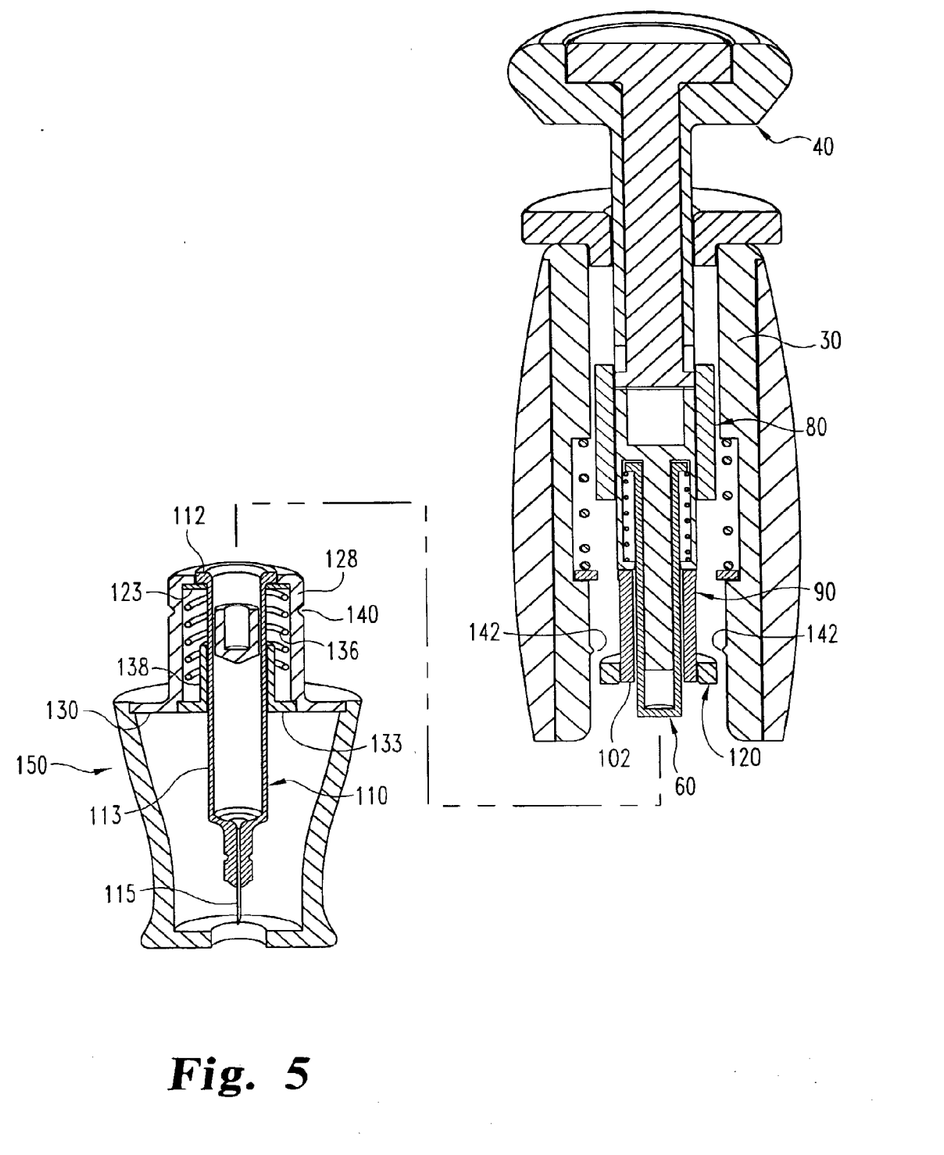
FIG. 5 is a cross-sectional front view of the delivery device of FIG. 1 prior to a replacement syringe mounting being completed.

As the shown delivery device 20 is to be reusable with, for example, replacement syringes, a plunger reset feature is provided, such as the reset collar assembly abstractly shown at 120. Reset collar 120 is mounted within housing body 30 to be axially and at least partially rotatably shiftable therein. When a user removes from housing body 30 the subassembly 150 and its held syringe 100 after an injection is complete, reset collar 120 is biased by a not shown spring of the assembly to a more proximal position within body 30, such as along a track/follower connection therebetween. During such proximal motion, or as caused by a spring force after such proximal motion is completed, the reset collar rotates relative to insertion sleeve 90. During such rotation, a not shown portion of the collar assembly 120, acting through, for example, an opening or slot provided in insertion sleeve 90, deactivates the latching of plunger extender 60 with plunger portion 50, thereby allowing reset spring 56 to automatically shift plunger extender 60 distally into bore 52. At the angular orientation resulting from this rotation, reset collar 120 engages insertion sleeve 90, via a not shown connection on its interior and on the exterior 104 of insertion sleeve 90. After a replacement syringe is installed in subassembly 150, such as by overcoming the friction fit of the existing syringe barrel with washer 123, removing the spent syringe, and then inserting a new syringe into frictional engagement with washer 123, the device is configured as shown in FIG. 5 Then, when subassembly 150 with its new syringe 110 is initially inserted distally into the proximal end of body 30, cup element 128 drivingly abuts the distal face of collar assembly 120, which in turn drivingly engages insertion sleeve 90. As the syringe and subassembly continue to be manually driven distally relative to body 30, reset collar 120 shifts insertion sleeve 90 distally until lock sleeve 80, due to its rotation forced by interaction with insertion sleeve 90, relatches with insertion sleeve 90. This rotation of lock sleeve 80, due to the interaction between tabs 76 and ramps 83, causes trigger 70 to reset distally within plunger 40. To further ensure trigger reset, the trigger may be provided with a spring biasing distally relative to the plunger shaft, which spring bias serves to shift the trigger distally when the previously plunged trigger is freed from, for example, its detent/indent connection to the plunger by a dedicated portion of the lock sleeve, at the start of lock sleeve rotation, camming a portion of the trigger other than its tab. When reset collar 120 has been shifted sufficiently to relatch insertion sleeve 90 with lock sleeve 80, reset collar 120 has been rotated, or is biased to rotate, relative to insertion sleeve 90 to an angular orientation allowing proximal motion of sleeve 90 relative to the collar assembly 120 during needle insertion. At such time, delivery device 20 is once again configured as shown in FIGS. 1 and 2 in a ready to insert orientation.

In an alternate embodiment, rather than having a reusable syringe mounting subassembly that is snap attached to a reusable body as described above, the reusable body of FIGS. 1-5 may be adapted to load disposable, syringe-equipped subassemblies from, and then back to after use, a protective storage container as is known in the art.

While this invention has been shown and described as having preferred designs, the present invention may be modified within the spirit and scope of this disclosure. For example, in an alternate embodiment, to prevent the plunger 40 from being plunged prior to the trigger 70 being actuated, and instead of the plunger physically abutting the distal face of the insertion sleeve to provide such prevention as shown, a plunger locking may be performed by a tab of the plunger that engages the lock sleeve, which locking engagement is deactivated during the rotation of the lock sleeve associated with trigger operation. This application is therefore intended to cover any variations, uses or adaptations of the invention using its general principles. Further, this application is intended to cover such departures from the present disclosure as come within known or customary practice in the art to which this invention pertains.

We claim:

1. A pharmaceutical delivery device comprising:
a housing having a first end and a second end spaced in an axial direction;
a pharmaceutical containing needled syringe mounted within said housing to be movable in said axial direction from a first position to a second position, wherein an injection tip of a needle of said needled syringe is recessed within said housing when in said first position and projects from said housing beyond said first end when in said second position;
a syringe advancing assembly operable to automatically advance said needled syringe from said first position to said second position; and
a plunger including an input portion projecting from said housing for manual access by a user, wherein said plunger is operable by the user directly shifting said input portion when said needled syringe is disposed in said second position to inject pharmaceutical from said needled syringe through said needle at a rate adjustably controlled by the user during said injection, wherein said plunger includes a plunger extender automatically movable within said housing from a first location to a second location upon said needled syringe advancing from said first position to said second position, wherein said plunger extender, when in said second location, occupies a space vacated by said needled syringe during advancement from said first position to said second position, whereby said plunger input portion remains stationary relative to said housing during said advancement of said needled syringe;
wherein said syringe advancing assembly comprises a trigger disposed on a distal end of said plunger input portion and axially depressible relative to said input portion to actuate said syringe advancing assembly; and
wherein said syringe advancing assembly comprises a lock member axially fixed within said housing, and an insertion member rotatably fixed within said housing and releasably engaged with said lock member, said lock member being angularly shiftable by said trigger during the depressing of said trigger to release said insertion member to allow a biasing member to shift said insertion member axially in a proximal direction to drive said needled syringe from said first position to said second position.

2. The pharmaceutical delivery device of claim 1 wherein said plunger input portion extends axially from a distal end of said housing.

3. The pharmaceutical delivery device of claim 1 wherein said plunger extender is operatively connected with said syringe advancing assembly to be advanced proximally in an amount and at a time the same as said needled syringe is advanced from said first position to said second position.

4. The pharmaceutical delivery device of claim 3 wherein said plunger extender and a shaft portion of said plunger comprise a telescopic connection, and wherein said extender and said plunger shaft portion are configured to axially fix said plunger shaft portion and said plunger extender together at the end of the advancement of said plunger extender with said needled syringe.

5. The pharmaceutical delivery device of claim 4 wherein a proximal end of said plunger extender fits within said syringe to directly abut a piston that sealing slides within a barrel of said syringe.

6. A pharmaceutical delivery device comprising:
a housing having a first end and a second end spaced in an axial direction;
a pharmaceutical containing needled syringe mounted within said housing to be movable in said axial direction from a first position to a second position, wherein an injection tip of a needle of said needled syringe is recessed within said housing when in said first position and projects from said housing beyond said first end when in said second position;
a syringe advancing assembly operable to automatically advance said needled syringe from said first position to said second position;
a plunger including an input portion projecting from said housing for manual access by a user, wherein said plunger is operable by the user directly shifting said input portion when said needled syringe is disposed in said second position to inject pharmaceutical from said needled syringe through said needle at a rate adjustably controlled by the user during said injection, wherein said plunger includes a plunger extender automatically movable within said housing from a first location to a second location upon said needled syringe advancing from said first position to said second position, wherein said plunger extender, when in said second location, occupies a space vacated by said needled syringe during advancement from said first position to said second position, whereby said plunger input portion remains stationary relative to said housing during said advancement of said needled syringe;
wherein said plunger extender is operatively connected with said syringe advancing assembly to be advanced proximally in an amount and at a time the same as said needled syringe is advanced from said first position to said second position; and
wherein said plunger extender and a shaft portion of said plunger comprise a telescopic connection, and wherein said extender and said plunger shaft portion are configured to axially fix said plunger shaft portion and said plunger extender together at the end of the advancement of said plunger extender with said needled syringe.

7. The pharmaceutical delivery device of claim 6 wherein a proximal end of said plunger extender fits within said syringe to directly abut a piston that sealing slides within a barrel of said syringe.

* * * * *

UNITED STATES PATENT AND TRADEMARK OFFICE
CERTIFICATE OF CORRECTION

| | | |
|---|---|---|
| PATENT NO. | : 7,918,824 B2 | Page 1 of 1 |
| APPLICATION NO. | : 11/915856 | |
| DATED | : April 5, 2011 | |
| INVENTOR(S) | : Steven Bishop et al. | |

It is certified that error appears in the above-identified patent and that said Letters Patent is hereby corrected as shown below:

On the Title page:
Insert -- (60) Related U.S. Application Data
Provisional application No. 60/692,437, filed on June 21, 2005 --

On the first page of the specification, insert the following cross-reference after the title:
-- This is the national phase application, under 35 USC 371, for PCT/US2006/023930, filed 19 June 2006, which claims the benefit, under 35 USC 119(e), of US provisional application 60/692,437, filed 21 June 2005. --

Signed and Sealed this
Twelfth Day of July, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,918,824 B2 | Page 1 of 1 |
| APPLICATION NO. | : 11/915859 | |
| DATED | : April 5, 2011 | |
| INVENTOR(S) | : Bishop et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 648 days.

Signed and Sealed this
Nineteenth Day of July, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,918,824 B2 | Page 1 of 1 |
| APPLICATION NO. | : 11/915859 | |
| DATED | : April 5, 2011 | |
| INVENTOR(S) | : Bishop et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 618 days.

Signed and Sealed this
Twenty-seventh Day of September, 2011

David J. Kappos
*Director of the United States Patent and Trademark Office*